US00PP33366P3

(12) United States Plant Patent
Hansen

(10) Patent No.: US PP33,366 P3
(45) Date of Patent: Aug. 17, 2021

(54) ***HIBISCUS* PLANT NAMED 'EVENING ROSE'**

(50) Latin Name: ***Hibiscus* hybrid (L.)**
Varietal Denomination: Evening Rose

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 75 days.

(21) Appl. No.: 16/602,618

(22) Filed: Nov. 8, 2019

(65) Prior Publication Data

US 2021/0144897 P1 May 13, 2021

(51) Int. Cl.
*A01H 5/02* (2018.01)
*A01H 6/60* (2018.01)

(52) U.S. Cl.
USPC ..... Plt./257
CPC ..... *A01H 6/608* (2018.05)

(58) Field of Classification Search
USPC ..... Plt./257
CPC ..... A01H 5/02
See application file for complete search history.

*Primary Examiner* — Kent L Bell

(57) ABSTRACT

A new and distinct cultivar of winter-hardy, herbaceous, perennial, hybrid *Hibiscus* plant named 'Evening Rose' comprising an upright, rounded, compact, mound habit of multiple, well-branched, mostly upright basal stems producing flowers from the bottom to the top of the plant for at least six weeks beginning mid-summer. Flowers have petals vivid purplish-red with deep red veins radiating to the margin and moderate red shiny eye surrounded by deep dark-red band set off with a deep red and white striped column displaying yellow-colored pollen. The foliage is mainly tri-lobed with burgundy color.

1 Drawing Sheet

Botanical classification: *Hibiscus* hybrid (L.).
Variety denomination: 'Evening Rose'.

STATEMENT REGARDING PRIOR DISCLOSURES UNDER 37 CFR 1.77(B)(6)

The first publically released non-enabling description was a photograph and brief description of the new plant was on Nov. 20, 2018 when it was featured as the August photograph in a 2019 calendar offer by Walters Gardens, Inc. The first disclosure, in the form of a sale, was made by Walters Gardens, Inc. on Apr. 1, 2019 to the wholesale grower Overdevest Nurseries L.P. followed by sales to other retail and wholesale nurseries by Walters Gardens, Inc. Walters Gardens, Inc. obtained the new plant and all information relating thereto, from the inventor. No plants of *Hibiscus* 'Evening Rose' have been sold, in this country or anywhere in the world, nor has any disclosure of the new plant been made, more than one year prior the filing date of this application, and such sale or disclosure within one year was either derived directly or indirectly from the inventor.

BACKGROUND AND ORIGIN OF THE PLANT

The present invention relates to the new and distinct hardy, herbaceous, *Hibiscus* plant, *Hibiscus* 'Evening Rose' hybridized under direction of the inventor on Aug. 5, 2015 at a wholesale perennial nursery in Zeeland, Mich. The new plant is a hybrid of the complex, unreleased, proprietary hybrid known as 12-231-1 (not patented) times 'Perfect Storm' U.S. Plant Pat. No. 27,880. Into the trial process the new plant was assigned the breeder code labeled 15-31-2. Both parents have a complex mixture of species in them, comprising the species: *moscheutos* and *coccineus*.

*Hibiscus* 'Evening Rose' was first asexually propagated in late summer of 2017 by sterile shoot-tip tissue culture and later by shoot tip cuttings at the same nursery in Zeeland, Mich. The resultant asexually propagated plants have been found to be stable and true to type in successive generations of asexual reproduction.

BRIEF SUMMARY OF THE PLANT

*Hibiscus* 'Evening Rose' differs from its parents as well as all other hardy herbaceous *Hibiscus* known to the applicant in many traits. The most similar *Hibiscus* known to the applicant are 'Jazzberry Jam' (not patented), 'Crown Jewels' U.S. Plant Pat. No. 11,857, 'Holy Grail' U.S. Plant Pat. No. 31,478, 'Berry Awesome' U.S. Plant Pat. No. 27,936, 'Summer in Paradise' U.S. Plant Pat. No. 28,730 and 'Mocha Moon' U.S. Plant Pat. No. 27,838. 'Jazzberry Jam' has flower of similar color, slightly larger, but lacks the deep burgundy-colored foliage and has a taller, less-rounded habit. 'Crown Jewels' is smaller in habit but lacks the burgundy-colored foliage, and the flower is white with pinkish veins and red center. 'Holy Grail' has primarily ovate foliage, and the flowers are deep reddish-colored. 'Berry Awesome' has dark green foliage rather than burgundy, the flowers are less puckered and flower color is lavender-pink. 'Summer in Paradise' is slightly shorter in habit, the foliage is olive green rather than deep burgundy, the flower is flatter with less puckering and the petals are a hot cerise-red. 'Mocha Moon' has a shorter habit, with more cupped flowers of white blushed in pink, with reddish centers and veins in the outer petal portion and the petals are less folded and less puckered. The female parent has flowers of a much deeper reddish coloration, with less folding of the petals, and the flower shape is deeper and more cupped.

Further comparison with the female parent is not possible since the plant was not maintained. The male parent, 'Perfect Storm', has a shorter more open habit, mostly tri-lobed foliage and the flower has a deeper red center eye and the base color is near white with pink veins.

*Hibiscus* 'Evening Rose' is a unique hardy herbaceous *Hibiscus* with the following combined traits:

1. Winter-hardy compact perennial with upright, round, mounded habit of multiple, well-branched, basal stems.
2. Many flat rotate flowers produced from bottom to top of plant.
3. Flowers produced for at least six weeks beginning mid-summer.
4. Flower petals of vivid purplish-red setting off a deep red and white striped column displaying yellow pollen.
5. Flower is slightly cupped with slight puckering in petals and leading edge folded underneath giving extra strength and support to flower.
6. Flower has a moderate-red shiny eye zone surrounded by deep dark red and deep red veins radiating to petal margins.
7. Foliage is mainly tri-lobed with strong burgundy color.

BRIEF DESCRIPTION OF THE DRAWINGS

The photographs of the new plant demonstrate the overall appearance of the plant, including the unique traits grown in Zeeland, Mich. The colors are as accurate as reasonably possible with color reproductions. Ambient light spectrum, source and direction may cause the appearance of minor variation in color.

DETAILED BOTANICAL DESCRIPTION

Figure 1:
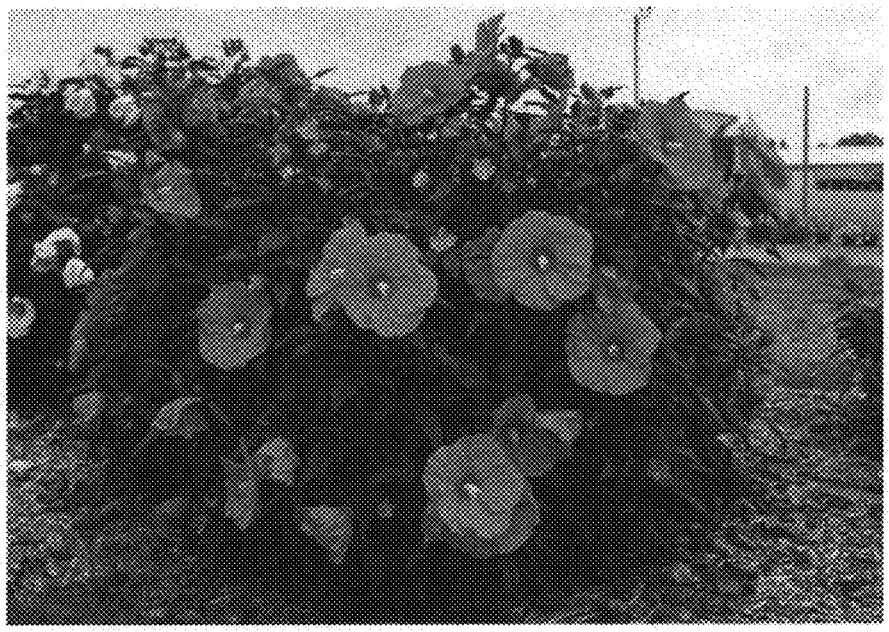
FIG. 1 shows a four-year-old plant in full flower in a trial garden.
Figure 2:
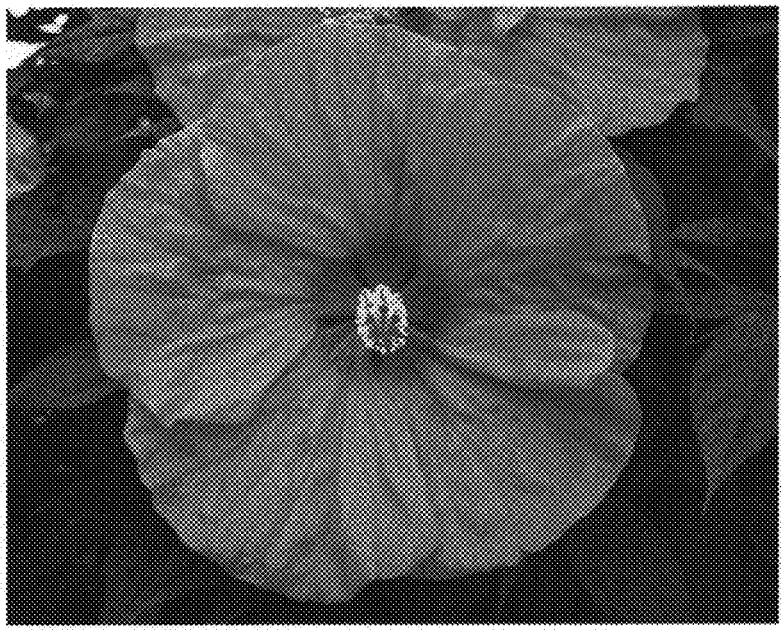
FIG. 2 shows a close-up of the flower.

The following descriptions and color references are based on the 2015 edition of The Royal Horticultural Society Colour Chart except where common dictionary terms are used. The new plant, *Hibiscus* 'Evening Rose', has not been observed under all possible environments. The phenotype may vary slightly with different environmental conditions, such as temperature, light, fertility, moisture and maturity levels, but without any change in the genotype. The following observations and size descriptions are of four-year-old plants in the loamy-sand, open-field full-sun trials of a nursery in Zeeland, Mich. with supplemental fertilizer and water as needed. The plants are of natural habit and were not treated with plant growth regulators, nor were they pinched at any time in the growth year.

Parentage: The female or seed parent is the unreleased, proprietary *Hibiscus* known by the breeder code 12-231-1, the male or pollen parent is 'Perfect Storm';

Propagation:

*Method.*—Shoot tip cuttings and sterile shoot-tip plant tissue culture division.

*Time to initiate roots from tissue culture.*—About two weeks.

*Rooting habit.*—Normal, branching, developing thick to about 2.5 cm diameter, fleshy; root color creamy yellow nearest RHS 161D depending on soil type.

*Crop time.*—Under normal summer growing conditions 12 to 16 weeks to flower in a four-liter container from cutting; plant vigor very good.

Plant description:

*Plant habit.*—Winter-hardy herbaceous perennial with about 38 thick, mostly upright, heavily-branched stems producing an upright spreading mound to about 143.0 cm tall and about 132.0 cm wide.

*Stem.*—Cylindrical, glabrous, glaucous; to about 143.0 cm tall and about 19.0 mm diameter at base, average about 133.0 cm tall and about 11.0 mm diameter at base.

*Stem color.*—Distally nearest RHS 187C, proximally nearest RHS 138B; Lateral branches: to 7 per stem, average about 5 per stem; cylindrical, glabrous, glaucous; to about 53.0 cm long and 6.0 mm diameter at base, smaller distally.

*Lateral branch color.*—Distally nearest RHS 187C, proximally nearest RHS 138B.

*Internode.*—About 26 nodes per stem below individual flowers; average internode length about 3.9 cm on unpinched plant.

*Internode color.*—Indistinguishable in color from surrounding stem.

Foliage description: Mostly tri-lobed, rarely 5-lobed; lobes dissected nearly to petiole; alternate; apex narrowly acute; base rounded to nearly cordate; margin coarsely and irregularly dentate; glabrous abaxial and adaxial; adaxial surface lustrous when expanding, slightly lustrous when mature, abaxial surface matte; leaf blades to about 19.0 cm long and about 18.5 cm across, average blade size 16.0 cm long and 16.0 cm wide; no fragrance detected;

*Foliage color.*—Young expanding leaves adaxial nearest 187A, abaxial nearest blend between RHS 146D and RHS 138B with irregular blushing typically around leaf margins nearest RHS 187B; mature leaves adaxial variable between RHS N186A and RHS 187A mottled with nearest RHS 137A and RHS NN137A, abaxial between RHS 147B and RHS 147C with light blushing distally nearest RHS 187A.

*Veins.*—Palmate; lustrous; costate on abaxial.

*Vein color.*—Young adaxial veins nearest RHS 187A with midrib nearest RHS 187A, abaxial veins nearest RHS 187C and midrib nearest RHS 187C; mature adaxial midrib nearest RHS 187C distally and proximally nearest RHS 184C with veins variable nearest RHS 187B and N187A, abaxial midrib nearest RHS N186C proximally and distally nearest RHS 184C, veins nearest RHS 187C.

*Petioles.*—Mostly cylindrical, proximally slightly applanate on adaxial side near base; glaucous; glabrous; to about 13.5 cm long and 6.5 mm diameter at base, average size about 8.6 cm long and 5.0 mm wide at base.

*Petiole color.*—Adaxial nearest RHS N186C, abaxial nearest RHS 146C blushed with nearest N186C.

Flower description: Complete; actinomophic; mostly outward facing; rotate; lasting up to two days on plant; to about 18.0 cm across and cupped to 6.0 cm deep, with column extending 40.0 mm long; flower size decreasing distally;

Buds one day prior to anthesis: Ellipsoidal with bluntly rounded apex and bluntly rounded base; sepals adpressed to petals; about 6.4 cm long and about 3.5 cm diameter in middle;

Bud seven days prior to anthesis, with petals still enveloped in calyx: Cylindrical with pointed apex and rounded base;

carinate at sepals fusion lines; glabrous, glaucous; about 2.7 cm long and about 1.8 cm across;

Bud color one day prior to anthesis: Exposed petal color distally nearest RHS 63C and proximally nearest RHS 56C;

Bud seven days prior to anthesis: Turbinate with sepal fusions carinate; color nearest blend of RHS 146D and RHS 145A with moderate blushing between carinae and heavy at carinae nearest RHS 187B;

Epicalyx: Typically 10 to 11 per flower; linear; entire, glabrous, with margin micro ciliate; dull surface abaxial and adaxial; narrowly acute apex and truncate base, distally arcuate toward apex; about 24.0 mm long and about 2.5 mm wide at base;

Epicalyx color: Adaxial and abaxial nearest RHS 146B with moderate to heavy blushing of nearest RHS N186C;

Calyx: Star-shaped hypanthium; campanulate; 22.0 mm long and 60.0 mm across;

Sepals: Five, fused in basal 12.0 mm and free in distal 25.0 mm; acute apex; glabrous; margin entire, edentate; abaxial and adaxial surfaces matte; individually about 35.0 mm long, about 17.0 mm wide at fusion;

Sepal color: Adaxial between RHS 146C and RHS 145A, veins nearest RHS 145B; abaxial between RHS 146C and RHS 145A blushed around veins nearest RHS 187C;

Flowers: Solitary, up to 40 per main stem without pinching; slightly cupped face; mostly outwardly facing; natural spread to about 18.0 cm across and 6.0 cm deep from stigma to base of calyx; smaller in later season;

Flower lastingness: Persist for one to two days; effective for at least six weeks beginning late July;

Flower fragrance: None detectable;

Petals: Five; glabrous; lustrous eye adaxial and abaxial; adnate to the androecium to form a column, imbricate to about 40% overlapping at widest part (petals overlapping 40% to the petals on either side); palmately veined, primary veins impressed on adaxial and slightly costate abaxial; surface slightly dimpled; rounded with distinct claw and limb; margins: entire, edentate; apex rounded; base short claw-like;

Petal size: Average about 12.0 cm across and about 9.5 cm long narrowing to claw base about 7.0 mm across (smaller in later part of flowering season);

Petal color: Adaxial central and distal region nearest RHS 61C, center eye 5.0 mm wide nearest RHS 45A, external to eye ring about 5.0 mm thick between RHS 59A and RHS 53A with next external ring about 10 mm thick of nearest RHS N45A on a base of nearest RHS 61C, veins nearest RHS 53A; abaxial basal 2.0 mm nearest RHS NN155D, distally blend between RHS 53C and RHS 61C with veins nearest RHS 53A;

Flower lastingness: One to two days;

Gynoecium: Single; partially enclosed in column;

*Column.*—Glabrous and lustrous; fringed distally with acute apices; about 40.0 mm long and about 11.0 mm across at base; with pistil exserted about 7.0 mm.

*Column color.*—Proximally between RHS 53A and RHS 53B, distally striated with between RHS 53A and NN155D, with apex nearest RHS 53A.

*Style.*—Micro-puberulent in region exserted above column, glabrous in region contained in column; about 4.7 cm long, basally penta-furcate in about distal 7.0 mm; branch diameter about 1.2 mm; color basally nearest RHS NN155D, distally transitioning to between RHS 61C and RHS 61B.

*Stigma.*—Typically five; flattened globose, puberulent, about 2.0 mm in diameter and 1.0 mm tall; color nearest RHS 59A.

*Ovary.*—Superior, ellipsoidal, rounded to broadly acute apex and flat truncate base; longitudinally fluted; about 11.0 mm across at base and about 9.0 mm tall; color nearest RHS 145C.

Androecium: Filaments: numerous, about 120; about 4.0 mm long and about 0.2 mm diameter; attached along nearly the entire length of column; color in distal portion of column nearest RHS NN155D and toward base of column between RHS N57B and RHS N57A;

*Anthers.*—Flattened reniform; dorsifixed; about 2.0 mm long and 1.0 mm across and thick; color nearest RHS 11B.

*Pollen.*—Abundant; color between RHS 11A and RHS 11B.

Pedicel: Cylindrical, glabrous, glaucous; upright, curved slightly outwardly; length from base of sepal to abscission point average about 4.8 cm long and 2.7 mm diameter, from abscission point to stem node about 15.0 cm long and about 4.0 mm wide; longer on early flowers and decreasing in distal flowers;

Pedicel color: Distal portion nearest N186C with blush of nearest RHS 146C, proximal portion nearest RHS 146B with blush of nearest RHS N186C;

Peduncle: Cylindrical, glabrous, glaucous; to about 143.0 cm long and 19.0 mm diameter at base, average 133.0 cm long and 11.0 mm diameter at base; flowering in the distal one-third; with up to seven branches that are up to 53.0 cm long;

Peduncle color: Distally nearest RHS 187C, proximally nearest RHS 138B;

Fruit: Penta-loculicidal capsule; pubescent along inner septa with hairs of nearest RHS 158A to about 4.0 mm long, glabrous outside; globose to ellipsoidal, cuspidate apex and flattened base; about 27.0 mm long and 26.0 mm diameter; color nearest RHS 200B when mature; about 40 to 50 seeds per fruit;

Seed: Minutely puberulent; globose; about 3.0 mm in diameter; color nearest RHS N199B;

Resistance: *Hibiscus* 'Evening Rose' has not displayed any pest and disease resistance beyond that typical of hardy perennial *Hibiscus*.

Growth requirements: The plant grows best with plenty of moisture.

Hardiness at least from USDA zone 4 through 9.

I claim:

1. A new cultivar of hardy herbaceous perennial *Hibiscus* hybrid plant named 'Evening Rose' as herein illustrated and described.

* * * * *